Figure 1:
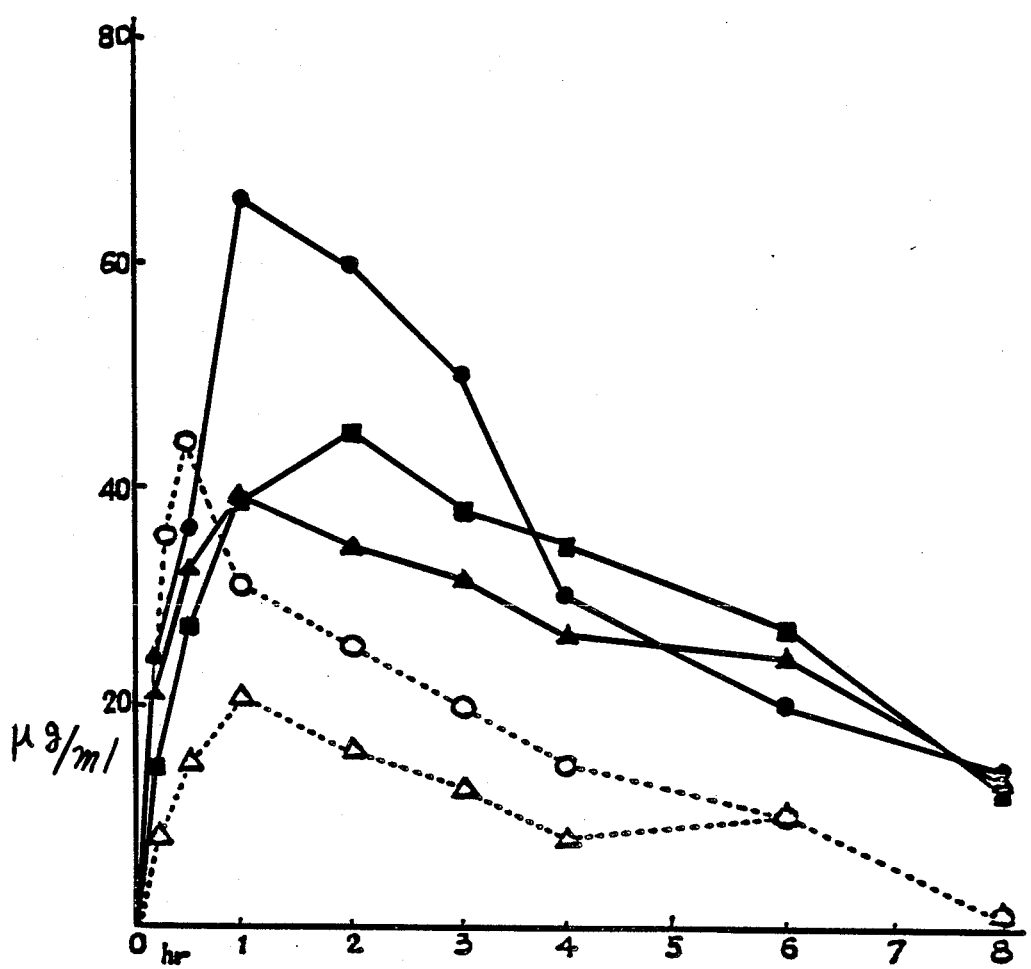

United States Patent [19]

Ushimaru et al.

[11] Patent Number: 4,874,774

[45] Date of Patent: Oct. 17, 1989

[54] NIFEDIPINE COMPOSITIONS AND THE PRODUCTION THEREOF

[75] Inventors: Koichi Ushimaru, Kamikyo; Tomoaki Hamakawa, Fushimi; Tomio Koga, Shiga, all of Japan

[73] Assignee: Nippon Shinyaku Co., Ltd., Japan

[21] Appl. No.: 895,806

[22] Filed: Aug. 12, 1986

Related U.S. Application Data

[63] Continuation of Ser. No. 670,547, Nov. 13, 1984, abandoned.

[30] Foreign Application Priority Data

Nov. 17, 1983 [JP]  Japan .................................. 58-217396

[51] Int. Cl.[4] .............................................. A61K 31/44
[52] U.S. Cl. ............................ 514/356; 424/DIG. 15; 514/929; 514/966
[58] Field of Search ....................... 514/356, 929, 966; 424/DIG. 15

[56] References Cited

U.S. PATENT DOCUMENTS

| | | |
|---|---|---|
| 2,538,127 | 1/1951 | Saunders et al. ............ 424/DIG. 15 |
| 3,485,847 | 12/1969 | Bossert et al. ....................... 546/321 |
| 4,364,952 | 12/1982 | Materne . |
| 4,368,185 | 1/1983 | Mizuno et al. .............. 424/DIG. 15 |

*Primary Examiner*—Allen J. Robinson
*Attorney, Agent, or Firm*—Jacobs & Jacobs

[57] ABSTRACT

Nifedipine is formulated into a reactally administrable composition for administration to humans and animals to effect coronary dilation and for hypotensive effect.

12 Claims, 1 Drawing Sheet

NIFEDIPINE COMPOSITIONS AND THE PRODUCTION THEREOF

This is a continuation of Ser. No. 670,547, filed Nov. 13, 1984, now abandoned.

The present invention relates to novel pharmaceutical compositions which contain nifedipine, i.e. 1,4-dihydro-2,6-dimethyl-4-(2'-nitrophenyl)-3,5-dicarbomethoxypyridine) in combination with a pharmaceutically acceptable carrier suitable for formulating rectally administrable compositions of nifedipine, as well as to methods of use of such compositions and processes for their production.

Nifedipine is known to exhibit coronary vasodilating action and hypotensive action and is an important pharmaceutical for use in the treatment of angina pectoris and hypertension. Heretofore, however, the disadvantage in administering nifedipine was that the compound is only sparingly soluble in water. Thus, it is difficult to formulate into an orally administrable form which can be readily absorbed by a human or animal.

In order to increase the absorption of nifedipine in the digestive organs of humans and animals and to improve its bio-availability, various pharmaceutical compositions have been tried. Such compositions may be divided into two types.

According to one of the types, nifedipine is treated in an attempt to make it more soluble. Such procedures are described in Japanese published Patent Applications 53/121921, 54/20127, 54/44034, 54/55713, 54/55714, 54/95721 and 56/115726.

The second procedure involves dissolving or dispersing nifedipine in a carrier such as a polymer so that the solubility of nifedipine is increased. Such a procedure is described in published Japanese Patent Applications 54/46837, 56/68619 and 57/85136.

The present invention is based on the discovery that absorption of nifedipine can be substantially improved by formulating it into a rectally administrable composition. Such a rectally administrable form overcomes the prior art problem of insufficient absorption and effectiveness and eliminates disadvantages of the prior art formulations which resulted in sudden decreases in blood pressure due to rapid increase of nifedipine in the bloodstream and accompanying undesired contraindications such as dizziness or giddiness. In addition, the disadvantage of too rapid metabolizing of nifedipine and its subsequent excretion which resulted in a rather short acting effect for prior art compositions of nifedipine has been overcome.

In addition, according to the prior art preparations, when nifedipine was administered at bedtime for the prevention of angina pectoris during sleeping, the results were not satisfactory and the length of availability of nifedipine in the patient receiving the preparation was not satisfactory. There were also problems in orally administering nifedipine to seriously ill patients who had difficulty swallowing.

It has therefore represented a substantial advance in the art to formulate nifedipine in a rectally administrable composition in which the nifedipine is easily absorbed and is maintained in the bloodstream for a sufficient period of time to effect a proper level of therapy.

The present invention comprises a pharmaceutical composition in rectal administration form which comprises a coronary vasodilating effective amount or a hypotensively effective amount of 1,4-dihydro-2,6-dimethyl-4-(2'-nitrophenyl)3,5-dicarbo-methoxypyridine) in combination with a pharmaceutically acceptable carrier suitable for formulating rectally administrable cmpositions. It has been found that the pharmaceutical compositions of the present invention are particularly suitable for rectal administration when the carrier is a base comprising a polyalkylene glycol and a suitable fatty oil which provides the proper suppository consistency. In such formulations, nifedipine is preferably contained in a base comprising 5 to 50 parts by weight of a polyalkylene glycol and from 50 to 95 parts by weight of a fat and oil. Preferred polyalkylene glycols are polyethylene glycol and polypropylene glycol. Polyethylene glycol having a molecular weight in the range of 200 to 20,000 is particularly preferred.

Examples of suitable fatty oils for use in the base of the pharmaceutical composition of the present invention are fatty acid glycerides, particularly those having 12 to 18 carbon atoms. Preferred glycerides include Adeps Solidus (German Pharmacopeia) and preparation similar thereto, such as, for example, Witepsol (Registered Trademark of Dynamit-Novel Company) of the types H, W, S, and E. In addition, cocoa butter and other vegetable fats and oils are hardened oils may be used. The fatty oils may be solid or semi-solid fats or liquid or semi-liquid oils.

The ratio of polyalkylene glycol to fat and oil is an important element of the present invention to ensure that there is both sufficient absorption of nifedipine and that the action of that substance is maintained in the bloodstream for a sufficient period of time. The above proportions, therefore, form an important element of the instant invention.

While the amount of nifedipine in each rectally administrable dosage unit may vary, it is generally preferred that each dosage unit contain from about 0.1 to about 5%, preferably from about 0.25 to about 2% by weight of nifedipine. In addition, the compositions of the present invention may contain other substances convention in the art such as nonionic surfactants, finely powdered silicic acid materials, cellulose derivatives and the like.

The present invention also includes a method of effecting coronary dilation in humans and animals and treating hypertension in humans and animals which comprises administering a coronary vasodilating effective amount or a hypotensively effective amount of 1,4-dihydro-2,6-(dimethyl-4-(2'-nitrophenyl)-3,5-dicarbo-meethoxypyridine in combination with a pharmaceutically acceptable carrier suitable for forming rectally administrable compositions. Since this method involves administration of the novel compositions of the present invention, the above described embodiments of the composition are, of course, important to and applicable for the method of use of the present invention.

The present invention also comprises a process for the production of the novel pharmaceutical compositions above described. This process for the production of a pharmaceutical composition in rectal administration form comprises combining a coronary vasodilating effective amount of a hypotensively effective amount of 1,4-dihydro-2,6-(dimethyl-4-(2'-nitrophenyl)-3,5-dicarbomethoxypyridine) with a pharmaceutically acceptable carrier suitable for formulating rectally administrable compositions which comprises from 5 to 50 parts by weight of a polyalkylene glycol and from 50 to 95 parts by weight of a fatty oil by:

(a) dissolving the desired amount of 1,4-dihydro-2,6-(dimethyl-4-(2'-nitrophenyl)-3,5-dicarbomethoxypyridine) in a polyalkylene glycol followed by mixing the solution with a suitable warm and melted fatty oil; or (b) adding the desired amount of 1,4-dihydro-2,6-(dimethyl-4-(2'-nitrophenyl)-3,5-dicarbomethoxypyridine) to and dissolving it into a warm and melted mixture of a polyalkylene glycol and a suitable fatty oil;

thereafter pouring the mixture into a suitable device for forming the rectally administrable form and allowing the same to cool.

The following non-limitative examples more particularly illustrate the present invention:

EXAMPLE 1

One gram of nifedipine is added to 21 grams of polyethylene glycol (400). The mixture was stirred until dissolution was complete. Eighty-four grams of Witepsol H-15 was melted at 45° C. and added to the solution. The resultant mixture was stirred and poured into a suppository mold for 2 gram preparations made by Erweka Co., and allowed to cool. The resultant nifedipine suppositories were suitable for rectal administration.

EXAMPLE 2

73.5 grams of Witepsol W-35 and 32 grams of polyethylene glycol (1500) were mixed and melted at 50° C. 0.5 grams of nifedipine was added thereto, the mixture was stirred until dissolution and worked up according to the procedure described in Example 1 to produce nifedipine suppositories.

EXAMPLE 3

42 grams of polyethylene glycol (1500) was melted at 50° C. and 1 gram of nifedipine was dissolved therein. 63 grams of Witepsol S-55 was melted at 50° C. and added thereto. The resultant mixture was stirred and worked up according to the procedure described in Example 1 to produce nifedipine suppositories.

EXAMPLE 4

31.5 grams of polyethylene glycol (1500) was melted at 50° C. and 1 gram of nifedipine was dissolved therein. 73.5 grams of Witepsol S-55 was melted at 50° C. and added thereto. The resultant mixture was stirred and worked up according to the procedure described in Example 1 to produce nifedipine suppositories.

EXAMPLE 5

21 grams of polyethylene glycol (1500) was melted at 50° C. and 1 gram of nifedipie was dissolved therein. 84 grams of Witepsol S-55 was melted at 50° C. and added thereto. The mixture was stirred and worked up according to the procedure described in Example 1 to produce nifedipine suppositories.

EXAMPLE 6

52.5 grams of Witepsol W-35 and 52.5 grams of polyethylene glycol (1540) were melted at 50° C. and 1 gram of nifedipine was added thereto. The mixture was stirred to form a solution and worked up according to the procedure described in Example 1 to produce nifedipine suppositories.

EXAMPLE 7

26.25 grams of polyethylene glycol (1500) was melted at 50° C. and 2 grams of nifedipine was dissolved thereon. 78.75 grams of Witepsol S-55 was melted at 50° C. and added thereto. The resultant mixture was stirred and worked up according to the procedure described in Example 1 to produce nifedipine suppositories.

EXAMPLE 8

42 grams of polyethylene glycol (1000) was melted at 50° C. and 1 gram of nifedipine was dissolved therein ater stirring. 63 grams of cacao butter was melted at 50° C. and was added thereto. The resultant mixture was stirred and worked up according to the procedure described in Example 1 to produce nifedipine suppositories.

The therapeutic effect of the compositions of the present invention is demonstrated by the test procedures set forth below. 2 gram suppositories containing 20 mg of nifedipine were prepared by dissolving nifedipine in a base comprising polyethylene glycol PEG-400: PEG-1500: PEG-6000 in a ratio of 3:3:4, by dispersing nifedipne in Witepsol S-55 base and in accordance with the procedures described in Examples 3, 4 and 5. Suppositories from each preparation were administered to beagle dogs weighing 10–11 kg, four dogs in each group, at a dosage of 2 mg/kg, rectally. Blood was collected from time to time and the nifedipine concentrations in the blood serum of the beagles were determined. The method of determination was the following: To the collected blood serum was added n-propyl p-hydroxybenzoate as an internal standard. Trichloroacetic acid was added to remove proteins, centrifugation was carried out and determined by high performance liquid chromatography (HPLC). The result is set forth in FIG. 1.

An area under the blood serum level curve for each preparation 8 hours after administration was measured and the area (AUC) was compared with another AUC when 2 mg/kg of an injectable solution prepared by dissolving nifedipine in a 50% aqueous polyethylene glycol solution was administered intravenously and the ratio calculated. The results are set forth in Table 1 below:

TABLE 1

|  | Ratio of areas under blood serum level curve* |
|---|---|
| Suppositories prepared from PEG base | 13.1 |
| Suppositories prepared from Witepsol S-55 | 9.3 |
| Suppositories of Example 3 | 31.0 |
| Suppositories of Example 4 | 26.6 |
| Suppositories of Example 5 | 23.9 |

*the case of intravenous injection was set at 100

From the results set forth in FIG. 1 and Table 1, it is clear that the nifedipine preparations according to the present invention exhibit a high blood serum level for a significant period of time as compared with the preparations prepared with only polyethylene glycol or only with a Witepsol base. The data clearly shows that as to bio-availability, the compositions of the present invention are 2 to 3 times more active than the comparison preparations.

FIG. 1 shows the mean value of the nifedipine level in the bloodstream when the nifedipine suppositories were rectally administered at a dosage of 2 mg/kg to beagles having a body weight of 10–11 kg (four dogs in each group). The ordinate and abscissa show blood serum level ($\mu$g/ml) and time elapsed (hours), respectively.

| — | Suppository prepared from polyethylene glycol only |
| Δ—Δ | Suppository prepared from Witepsol S-55 base only |
| — | Suppository prepared according to Example 3 |
| — | Suppository prepared according to Example 4 |
| — | Suppository prepared according to Example 5 |

The preferred dosage range for humans and animals for the nifedipine suppositories of the present invention is from about 0.06 mg/kg to about 2 mg/kg per day. It will be appreciated that the amount may be greater or lesser depending upon such factors as the severity of the condition, the past medical history, the age and general health condition of the patient and the physician's sound judgement.

What we claim is:

1. A pharmaceutical composition in rectal administration form which comprises a coronary vasodilating effective amount or a hypotensively effective amount of 1,4-dihydro-2,6-dimethyl-4-(2'-nitrophenyl)3,5-dicarbomethoxy-pyridine in combination with a pharmaceutically accepable carrier suitable for formulating rectally administrable compositions which comprises a mixture of 5 to 50 parts by weight of a polyethylene glycol and 50 to 95 parts by weight of a fatty acid glyceride of 12 to 18 carbon atoms.

2. A composition according to claim 1 wherein the polyethylene glycol has a molecular weight of from 200 to 20,000.

3. A composition according to claim 1 which contains from about 0.1 to about 5% by weight of 1,4-dihydro-2,6-dimethyl-4-(2'-nitrophenyl)-3,5-dicarbomethoxypyridine.

4. A composition according to claim 1 which contains from about 0.25 to about 2% by weight of 1,4-dihydro-2,6-dimethyl-4-(2'-nitrophenyl)-3,5-dicarbomethoxypyridine.

5. A method of effecting coronary vasodilation in humans and animals which comprises rectally administering to a human or animal in need thereof a pharmaceutical composition which comprises a coronary vasodilating effective amount of 1,4-dihydro-2,6-dimethyl-4-(2'-nitrophenyl)3,5-dicarbo-methoxypyridine in combination with a pharmaceutically acceptable carrier suitable for formulating rectally administrable composition which comprises a mixture of 5 to 50 parts by weight of a polyethylene glycol and 50 to 95 parts by weight of a fatty acid glyceride of 12 to 18 carbon atoms.

6. A method according to claim 5 wherein the polyethylene glycol has a molecular weight of from 200 to 20,000.

7. A method according to claim 5 which comprises rectally administering suppositories wherein each suppository contains from about 0.1 to about 5% by weight of 1,4-dihydro-2,6-dimethyl-4-(2'-nitrophenyl)-3,5-dicarbomethoxypyridine.

8. A method according to claim 5 which comprises rectally administering suppositories wherein each suppository contains from about 0.25 to about 2% by weight of 1,4-dihydro-2,6-dimethyl-4-(2'-nitrophenyl)-3,5-dicarbomethoxypyridine.

9. A method of treating hypertension in humans and animals which comprises rectally adminstering to a human or animal in need thereof a pharmaceutical composition which comprises a hypotensively effective amount of 1,4-dihydro-2,6-di-methyl-4-(2'-nitrophenyl)3,5-dicarbo-methoxy-pyridine in combination with a pharmaceutically acceptable carrier suitable for formulating rectally administrable composition which comprises a mixture of 5 to 50 parts by weight of a polyethylene glycol and 50 to 95 parts by weight of a fatty acid glyceride of 12 to 18 carbon atoms.

10. A method according to claim 9 wherein the polyethylene glycol has a molecular weight of from 200 to 20,000.

11. A method according to claim 9 which comprises rectally administering suppositories wherein each suppository contains from about 0.1 to about 5% by weight of 1,4-dihydro-2,6-dimethyl-4-(2'-nitrophenyl)-3,5-dicarbomethoxypryidine.

12. A method according to claim 9 which comprises rectally administering suppositories wherein each suppository contains from about 0.25 to about 2% by weight of 1,4-dihydro-2,6-dimethyl-4-(2'-nitrophenyl)-3,5-dicarbomethoxypyridine.

* * * * *

UNITED STATES PATENT AND TRADEMARK OFFICE
CERTIFICATE OF CORRECTION

PATENT NO. : 4,874,774

DATED : October 17, 1989

INVENTOR(S) : KOICHI USHIMARU ET AL

It is certified that error appears in the above-identified patent and that said Letters Patent is hereby corrected as shown below:

Column 5, line 1, change "——" to -- o ---O--;

Column 5, line 3, change "——" to -- ● ---●--;

Column 5, line 4, change "——" to --■ ---■--; and column 5, line 5, change "——" to --▲---▲--.

Signed and Sealed this

Fifth Day of March, 1991

*Attest:*

HARRY F. MANBECK, JR.

*Attesting Officer*  *Commissioner of Patents and Trademarks*